United States Patent [19]

Schäfer et al.

[11] Patent Number: 4,908,206
[45] Date of Patent: Mar. 13, 1990

[54] EXTRACTS OF EMBRYONIC ORGANS, PROCESS FOR THEIR PREPARATION AND PHARMACEUTICAL PREPARATION CONTAINING THEM

[75] Inventors: Rolf Schäfer; Hans Hitz, both of Arisdorf, Switzerland

[73] Assignee: Amics AG, Oberwil, Switzerland

[21] Appl. No.: 95,581

[22] Filed: Sep. 10, 1987

[30] Foreign Application Priority Data

Sep. 16, 1986 [CH] Switzerland .................. 3724/86

[51] Int. Cl.$^4$ .................. A61K 35/54; A61K 35/23; A61K 35/34; A61K 35/407
[52] U.S. Cl. .................. 424/95; 424/103; 424/106; 424/104; 424/105; 514/859; 514/878
[58] Field of Search .................. 424/95, 103–106; 514/859, 878

[56] References Cited

U.S. PATENT DOCUMENTS

| | | | |
|---|---|---|---|
| 1,968,605 | 7/1934 | Jablons et al. | 424/103 |
| 2,358,869 | 9/1944 | Maurer et al. | 424/106 |
| 2,912,359 | 11/1959 | Angstein et al. | 424/101 |
| 3,172,813 | 3/1965 | Daniels et al. | 424/103 |
| 3,953,290 | 4/1976 | Uthne et al. | 514/2 |
| 3,973,001 | 8/1976 | Jaeger et al. | 424/101 |
| 4,054,557 | 10/1977 | Sievertsson | 514/2 |
| 4,139,611 | 2/1979 | Wacker et al. | 424/101 |
| 4,220,642 | 9/1980 | Said et al. | 514/2 |

FOREIGN PATENT DOCUMENTS 0038511 10/1981 European Pat. Off.

OTHER PUBLICATIONS

Bourland et al., cited in Chem. Abstracts, vol. 67: 111419w, 1967.
Jabaily et al., cited in Biol. Abstracts, vol. 66, No. 69542, 1978.
Dictionary Vidal, 1974, p. 631, O.V.P. Paris, "Extrait de coeur embryonnaire Mauchant".

*Primary Examiner*—Jacqueline M. Stone
*Attorney, Agent, or Firm*—Allegretti & Witcoff, Ltd.

[57] ABSTRACT

From organs of embryonic mammalia a new extract of active ingredients is recovered which extract can be used for controlling a reduced blood flow through periperhic organs and through the brain and which extract can be also used for controlling acne vulgaris. The corresponding extracts are used as active ingredients of corresponding pharmaceutical preparations.

The new pharmaceutically active extract is prepared according to a process in which polar substances having a molecular weight below 5000 are isolated from the embryonic mammalian organs avoiding any degradation of substances having a higher molecular weight. The finely divided embryonic mammalian organs are extracted with a mixture of water and a water soluble organic solvent which contains not more than 30 vol.-% of water at an about neutral pH value for stirring and refluxing. The resulting solution is then submitted to a predetermined sequence of further drying steps, heating steps and cooling steps, and finally to a filtration with an ultramembrane filter in order to remove any substances having a molecular weight of about 5000. The extract is then finally concentrated under vacuum to yield a liquid concentrate or a dry residue.

18 Claims, No Drawings

EXTRACTS OF EMBRYONIC ORGANS, PROCESS FOR THEIR PREPARATION AND PHARMACEUTICAL PREPARATION CONTAINING THEM

BACKGROUND OF THE INVENTION

The present invention concerns a new process for the preparation of an extract of embryonic mammalian organs, which extract is free of nonpolar constituents and constituents having a high molecular weight. The extract is prepared according to a new extraction process in which the first extraction step of the finely divided embryonic organs is performed with a mixture of water and a water miscible organic solvent, which mixture contains at least 70 vol.-% referred to the total volume of said mixture of the water miscible organic solvent and has an about neutral pH-value in order to avoid degradation of high molecular proteins. The recovered extract, accordingly, contains only such polar constituents having a molecular weight of lower than 5000 which had been present in the fresh embryonic mammalian organs and no materials produced through a degradation of proteinous constituents.

The produced extracts are used as active ingredients of pharmaceutical preparations for the treatment of reduced blood flow through the brain or peripheric organs and as active ingredient of pharmaceutical preparations for the treatment of acne vulgaris.

DESCRIPTION OF THE PRIOR ART

It is well known in the art that from mammalian blood and mammalian organs there can be recovered pharmaceutically active ingredients which can be used for the treatment or the prophylactic treatment of several ill conditions.

In the U.S. Pat. Nos. 3,953,290 and 4,054,557 there are disclosed processes for recovering polypeptides which promote the growth of cells and which have a molecular weight in the range of 4000 to 7000. Said polypeptides are recovered from a blood plasma or blood serum of mammalia by a treatment with acid, preferably hydrochloric acid.

The U.S. Pat. No. 4,139,611 discloses a process for the preparation of polypeptides having an insulin-like activity by submitting blood or blood components to a hydrolysis either in the acidic pH range of 2-4 or in the alkaline pH range of 8-10. According to said process from the hydrolyzate there is recovered by dialysis a corresponding polypeptide fraction having a molecular weight in the range of 350 to 6000.

In the U.S. Pat. No. 2,912,959 there is described a process according to which hemolyzed blood is submitted to hydrolysis with a proteolytic enzyme, like papain, in order to produce a material which is free of proteins and which has a wound healing activity.

The U.S. Pat. No. 3,973,001 discloses a process for recovering from the blood of young mammalia like e.g. one month old calves a blood extract which has a cell respiration stimulating activity and cell growth stimulating activity. According to said process the blood is defibrinated, hemolyzed and free of any solid constituents and from said solution there are removed by dialysis those components which have a molecular weight of above 4500.

In the French patent publication No. 2,157,994 there is furthermore described a product for treating disorders and illnesses of the system of peripheric blood vessels, according to which process the pharmaceutically active ingredients are isolated from the fats of the bone marrow of mammalia.

Also processes for isolating active ingredients from single organs of mammalia are already known in the art.

In the European patent publication No. 0,038,511 there is described a wound healing composition which contains active ingredients which are isolated from blood, blood plasma, serum or tissues of mammalia. The corresponding process comprises a step in which the material is treated with acetic acid or alternatively one step in which the material is treated with hydrochloric acid and a further step in which it is treated with sodium hydroxide.

In the U.S. Pat. No. 4,220,642 there is described a process for extracting and isolating peptides of the lungs of animals according to which process the first extraction step is performed under acidic conditions using acetic acid.

In the French medicament patent (brevet spécial de médicaments) no. 1951 M there is described a pancreas extract which is used for the treatment of chronical and acute illnesses of the vessels. The mammalian organs are deep-frozen, diminuted mechanically and lyophilized in the deep-frozen state. On page 2, left column, third paragraph of said patent there is explained that according to prior art processes from organ extracts proteins had been removed by acidifying said extracts and heating them in the presence of alcoholic solvents in order to precipitate said proteins.

In the French medicament patent no. 1953 M there is described a lung extract which influences the metabolism of fats and which can be used for treating tuberculosis. It is explained on page 1, right column, lines 3-5 of said patent that during the preparation of the extract any heating steps and also a treatment with water miscible solvents has to be strictly avoided.

The international patent publication No. WO-A-81/01,514 concerns a cosmetical preparation for the treating of the skin which contains as active ingredient a water soluble extract of spleen or liver which extract preferably contains the water soluble low molecular constituents and is specially preferred essentially free of any proteins. The organs are extracted with an aqueous extraction medium and the proteins precipitated from the aqueous extract by adding a water miscible organic solvent.

The corresponding extracts enhance the oxygen uptake of the skin.

In the French patent publication No. 2,320,760 there is described a pharmaceutical preparation which can be used for several purposes including a treatment of illnesses of the blood vessels and disorders of the brain caused by advanced age. The preparations contain a mixture of gangliosides which was recovered by treating nerve tissue of animals with a phosphate puffer in the presence of tetrahydrofurane. The solid constituents are then removed by centrifuging and the non-polar constituents removed using diethylether. Finally the product is purified by applying it to a column filled with ion exchangers. Research works which were performed sometime later showed that because of the complex composition of extracts of animal organs it is very disadvantageous to treat such extracts with ion exchangers.

The German Offenlegungsschrift 1,910,715 discloses a fraction having antimicrobial activity which was isolated from brains and the spleens of mammalia. Said fraction has a molecular weight in the range of 1000 to 2000 and it was isolated by extracting the starting material with alcohol removing the alcohol from the extracts and performing a gel filtration using an aqueous solution having a pH value in the range of 4–5.

In the European patent publication No. 140,134 there is described a process for the preparation of a biologically active extract of mammalian organs and cell cultures. Said extract contains the biologically active substances which have a molecular weight of below 10,000 daltons. The diminuted cells are dispersed in water without any organic solvents or other substances being added and said dispersion is then rapidly heated to a temperature of 70° to 90° C., the solid constituents removed and discarded and the solution submitted to an ultrafiltration in order to remove substances having a molecular weight of more than 10,000 daltons. The used mammalian organs, like the thymus, can be from young animals, like calves. No reference, however, is made to any embryonic organs. The corresponding extracts are able to normalize the propagation of fibroplasts which previously had been damaged.

In the German Offenlegungsschrift No. 3,524,794 there is described a pharmaceutical preparation which contains living reproducible embryonic cells of mammalia in a liquid or solid inert medium. If said preparations are administered adult human beings then several days after the administration in the serum of the treated person there are to be found cell regenerating substances which are able to regenerate prior damaged cells of cell cultures containing mammalian cells.

In the DICTIONNAIRE VIDAL, 1974, page 631, O.V.P., Paris, FR; "Extrait de coeur embryonnaire Mauchant" there is described an extract of the hearts of embryonic calves complexed with adenosine monophosphoric acid. It is stated that said enzyme complex can control the function of the heart and the regeneration of it. Nothing is stated about the process for the preparation of the complex of said embryonic heart extract.

In the German Offenlegungsschrift No. 1,467,791 there is described a process for the preparation of an extract of embryonic organs. According to said process three extraction steps are performed, i.e. an extraction step in the neutral pH range which is preferably performed using water or an aqueous buffer solution, a second extraction step performed in the basic pH range and a third extraction process performed in the acidic pH range. The three extracts are preserved separately and finally combined with each other. Also corresponding extracts of the organs of adult animals and of the placenta are described. It is stated only that these extracts can be used as component of pharmaceutical compositions. The publication is silent as to the pharmaceutical activity the extract in question should have.

In the French patent publication No. 2,332,760 there is described a process for the extraction of the skin of embryonic calves. The extraction of the skin is performed with an acidic aqueous solution which preferably has a pH value in the range of 3–5, at a temperature in the range of 60°–75° C. The corresponding extracts can be used as components of pharmaceutical and cosmetical compositions.

SUMMARY OF THE INVENTION

The object of the present invention was to produce new extracts from embryonic mammalian organs by submitting said organs to a new extraction procedure. According to said process the finely divided embryonic organs are extracted with an extraction medium which has an about neutral pH value and which is a mixture of water and at least 70 vol.-%, referred to the total volume of the extraction medium of a water miscible organic solvent. During the extraction process and the further purification steps any acidic pH ranges or basic pH ranges as well as the addition of enzymes should be avoided in order to prevent proteins of high molecular weight from being degraded to proteins having lower molecular weight.

A further object of the present invention is to remove from the extracts any material having a molecular weight of more than 5000 as well as any non polar materials.

DESCRIPTION OF THE INVENTION

One object of the present invention is a process for the preparation of an extract of finely divided mammalian organs wherein as extraction medium there is used a mixture of water and water soluble solvent and which extract is free of nonpolar constituents and constituents having a high molecular weight.

Said process is characterized in that the used mammalian organs or mixture of mammalian organs are organs of embryonic mammalian and that the finely divided organs are dispersed in a mixture of water and a water miscible organic solvent, which mixture has a pH value in the range of 6–8 and contains at least 70 vol.-%, referred to the total volume of said mixture, of the water miscible organic solvent and where the dispersion is vigorously stirred and refluxed at the pressure of the environment for at least two hours and thereafter the dispersion is cooled to a temperature of below +8° C. and the liquid medium separated at a temperature of below +8° C. from the solid constituents which are discarded, and that thereafter the aqueous organic solution is evaporated under vacuum to leave a dry residue, which residue is diluted with water and stirred at a temperature in the range of 75°–85° C. for 30 minutes to two hours and thereafter again cooled to a temperature of below +8° C. and maintaining said temperature the solid constituents are removed from the solution and discarded and that finally from the solution any constituents having a molecular weight of more than 5000 daltons are removed by ultrafiltration using an ultramembrane filter.

According to said new extraction process therefore an extract is recovered which contains only such substances which were originally present in the fresh finely divided embryonic organs. During all steps of the new process acidic pH ranges and alkaline pH ranges are avoided in order to prevent that proteins having a high molecular weight are hydrolyzed to yield proteins having a low molecular weight. Process steps are performed in order to remove from the extract any substances having a molecular weight of more than 5000 daltons and to remove from the extract unpolar substances. Said process steps are easily performed. The disadvantages of a fractionation performed with a column filled with ion exchangers are avoided and also the time consuming process steps which are necessary if a gel filtration is made.

The new process yields a new extract of embryonic mammalian organs, which extract contains only such active ingredients of low molecular weight which are relatively polar and which had been present in the organs of the embryonic mammalians.

According to the new process there are recovered from about 1000 parts by weight of the fresh embryonic organs used as starting materials 4–11 parts by weight of a dry extract of pharmaceutically active ingredients. The process for preparing said pharmaceutically active extract of embryonic organs can be performed relatively simply and any time consuming and complicated processes like fractionations using columns filled with ion exchangers and gel filtrations are avoided.

A further object of the present invention is to provide pharmaceutical preparations for the treatment of reduced blood flows through the brain or peripheric organs, also pharmaceutical preparations for the treatment of acne vulgaris. Said pharmaceutical preparations contain as active ingredient the extracts of embryonic mammalian organs prepared according to the new process, which extracts are free of nonpolar constituents and constituents having a high molecular weight.

According to a preferred embodiment of the inventive process the extraction step is performed using a mixture which contains 75 vol.-% to 85 vol.-%, referred to the total volume of said mixture, of a water miscible organic solvent selected from the group which comprises methanol, ethanol, propanol and acetone. Probably the dispersion of the finely divided embryonic organs in the mixture of water and water miscible organic solvent has a pH value in the range of 6.5–7.5, specially preferred a pH value in the range of 6.8–7.1.

A specially preferred extraction medium for the performance of the extraction step is a mixture of 80 vol.-% of ethanol plus 20 vol.-% of water and the dispersion of the finely divided embryonic organs in said solvent mixture has a pH value in the range of 6.5–7.5, preferably a pH value in the range of 6.8–7.2.

When the extraction step of the inventive process is performed then preferably per part by weight of the fresh finely divided embryonic organs there are added 5 parts by weight to 15 parts by weight of the mixture of water and water miscible organic solvent. It is specially preferred to use per part by weight of the finely divided embryonic organs or a mixture of different finely divided embryonic organs 9 to 10 parts by weight of the mixture of water and water miscible organic solvent.

The preferred embryonic organs are isolated from embryos which were recovered after the embryo matured to one half to 5/6 of the usual gestation period.

Preferred mammalia of which the embryonic organs are used in the inventive process are ruminants, preferably embryonic calves, sheep or goats. Examples of further mammalia, the embryonic organs of which can be used for the preparation of the inventive pharmaceutical preparations are horses, swine, monkeys and rodents like rabbits and guinea-pigs.

The preferred embryonic organs which are used for the preparation of the inventive pharmaceutically active extracts are lungs, kidneys, livers and hearts or mixtures of different organs of the embryonic mammalia, which mixtures however preferably contain at least one of the above stated organs.

Tests which were performed with different parts of the embryonic organism showed that corresponding extracts which were recovered from the blood of the embryos, the bone marrow of the embryos and embryonic glands which produce hormones and enzymes, like the pancreas, do not yield extracts which have the desired pharmaceutical activity and said parts of the embryonic mammalia accordingly cannot be used for the preparation of the inventive extracts. Quite unexpectedly it furthermore was also found out that the corresponding organ extracts which were produced from the brains of the mammalian embryos did not have the desired pharmacological activity, i.e. they were not active in enhancing reduced blood flows through the brain or peripheric organs and they also showed no pharmaceutical activity in the treatment of acne vulgaris.

When embryonic organs are used for performing the inventive process first any remaining residues of tissue which do not belong to the corresponding organ as well as particles of fat, are removed. Thereafter the corresponding organs or mixtures of different organs are comminuted, preferably already in the mixture of water and water miscible organic solvent with which the first extraction step is performed.

It was found out that it is specially advantageous to use different organs of the corresponding mammalian embryos and to comminute or crush said different organs together in the solvent mixture. The dispersion of the mammalian organs in the solvent mixture is then submitted to the following process steps.

The dispersion of the finely divided embryonic organs in the mixture of water miscible organic solvents and water has to be vigourously stirred and refluxed at the pressure of the environment for at least two hours. Preferably said dispersion, for example a dispersion in a mixture of 20 vol.-% of water and 80 vol.-% of ethanol, is refluxed for 2.5 hours to 3.5 hours, for example for three hours. During said refluxing step high molecular protein constituents are precipitated. It is essential that during said refluxing step the pH value of the dispersion is maintained in an about neutral pH range, so that a hydrolytic degradation of the high molecular proteins of the extracts to yield proteins of lower molecular weight or peptides or single amino acids is prevented. Preferably the refluxing step is performed while maintaining the pH of the dispersion in the range of 6.5 to 7.5 and specially preferred in the range of 6.8 to 7.1.

After said refluxing step the suspension is cooled to a temperature of 8° C. or below, for example to a temperature in the range of +2° C. to +6° C., and the solid constituents are separated from the cooled suspension or dispersion. Solid constituents can e.g. be removed by filtration or centrifuging and the solids are discarded.

The aqueous organic solution is thereafter evaporated under vacuum to yield a dry residue. Said dry residue is yellowish brown and usually from 1000 parts by weight of the finely divided embryonic organs there are recovered 5 to 12 parts by weight, preferably 7 to 10 parts by weight, of said dry residue.

The dry residue is then mixed with water and stirred at a temperature in the range of 75° to 85° C. for 30 minutes to two hours and thereafter again cooled to a temperature of 8° C. or below. Preferably per part by weight of the dry residue 100 to 150 parts by weight, specially preferred 120 to 130 parts by weight, of water are added.

The stirring is preferably performed at a temperature in the range of 77° to 83° C. and preferably the agitating of the mixture maintaining said temperature is performed for about one hour. It is essential that also during said second heat treatment the pH value of the aqueous medium is maintained in the range of 6.5 to 7.5, preferably 6.8 to 7.1, in order to avoid that in said step of the inventive process any high molecular proteins are degradated yielding proteins of lower molecular weight, peptides or amino acids.

After said heat treatment the solution is cooled to a temperature of +8° C. or below, preferably to a temperature in the range of 2° C. to 6° C. During said cooling step the yellowish solution gets turbid.

The solid constituents are removed from the cooled turbid solution, for example by filtration, e.g. by a filtration through a glass-frit.

The resulting clear solution is then filtered through an ultramembrane filter having an exclusion limit of 5000 daltons. Said ultrafiltration is not very timeconsuming and through said process steps any products having a molecular weight of more than 5000 are removed from the solution.

Preferably said ultrafiltration is performed by filtering first ⅔ to 5/6 of the total volume of the solution through said ultramembrane filter and by diluting the not yet filtrated part with water to a volume which corresponds to the starting volume. Then ⅔ to 5/6 of said diluted materials are filtered through said membrane filter. Optionally the remaining not yet filtered solution can again be diluted to the original starting volume and once more ⅔ to 5/6 of said second diluted solution filtered through the ultramembrane filter. This step can optionally be once more repeated.

If the filtration through the ultramembrane filter is performed according to the above stated preferred embodiment then the volume of water compared with the quantity of water in which the dry residue had been dissolved is increased to twofold or threefold volume. If accordingly one part by weight of the dry residues had been mixed with 100 to 150 parts by weight of water then after said ultrafiltration one part by weight of the dry residue is dissolved in 200 to 450 by weight of water.

For many fields of application said solution is too diluted and according to a preferred embodiment of the claimed process said aqueous solution is therefore concentrated under vacuum until a concentrated extract or a dry residue is produced. Preferably after the ultrafiltration the aqueous solution is first concentrated under vacuum until its volume has reached one tenth of the volume of the ultrafiltrate. Thereafter said concentrated solution is preferably lyophilized to yield a yellowish dry residue.

Per 1000 parts by weight of the used fresh embryonic organs usually 3 to 10 parts by weight, for example 5 to 8 parts by weight, of said yellowish dry residue are recovered.

If said dry residue is dissolved in water then the aqueous solution is clear and not at all turbid. Said aqueous solution was tested by a gel electrophoresis and no proteins having a molecular weight of more than 5000 could be detected.

Furthermore the final product was submitted to antigen tests and said tests proved that the product is free of any substances which could provoke allergies.

Inventive pharmaceutical preparations for the treatment of reduced blood flows through the brain and peripheric organs, respectively inventive pharmaceutical preparations for the treatment of acne vulgaris contain as active ingredient the extract of embryonic organs prepared according to the inventive process and optionally furthermore a pharmaceutically acceptable carrier or diluent.

The corresponding pharmaceutical preparations can be formulated so that they are suited for an oral administration, an administration via injection or infusion or for a topic 21 administration.

It was quite unexpectedly found that human persons which suffered from diabetes and which were treated with the inventive pharmaceutical products noticed a clear mitigation of their diabetic condition. This also was proved by a urine or blood test of said persons. It is likely that the extracts of embryonic organs prepared according to the inventive process can be also used as active ingredient of pharmaceutical preparations for the treatment of diabetes.

For testing the pharmaceutical activity of inventive pharmaceutical preparations for controlling acne vulgaris female and male persons which mainly were 16 years old to 21 years old were tested and all tested persons suffered from acne vulgaris. The tests were performed by applying the pharmaceutical preparations topically to the skin and also by administering corresponding pharmaceutical preparations orally.

The pharmaceutical preparations for controlling reduced blood flow through peripheral organs were tested on female and male persons most of which were 40 years to 60 years old. All the tested persons suffered from the symtoms of reduced blood flow through peripheral organs. Several groups of persons were tested and the corresponding pharmaceutical preparations were administered in said groups either orally or by injection or also topically.

The pharmaceutical activity of inventive pharmaceutical preparations for the treatment of reduced blood supply to the brain was tested with groups of male and female persons most of which were 60 to 75 years old. The corresponding pharmaceutical preparations were administered to the tested persons either orally or by injection.

The following examples illustrate the inventive process for the preparation of the pharmaceutically active extracts of embryonic mammalian organs. Furthermore the following examples show the results of tests indicating the pharmaceutical activity of the recovered extracts. Said examples will serve only to further illustrate and not limit the invention.

EXAMPLE 1

Preparation of a pharmaceutically active extract of organs of embryonic calves 10 kg of a mixture of lungs, kidneys, livers and hearts of embryonic calves were comminuted together, for example by passing them through a mincing machine.

The resulting paste or mash of embryonic organs was added to 100 l of mixture of 20 vol.-% of water plus 80 vol.-% of ethanol. Said slurry was vigorously stirred and refluxed under the pressure of the environment for three hours.

Thereafter the slurry was rapidly cooled to a temperature of 4° C. and the solid constituents of said slurry were removed by centrifuging. The supernatant liquid was separated from the sediment layer of solid material and the solid material discarded.

The aqueous alcoholic liquid was concentrated under vacuum using a water jet vacuum pump and a rotary evaporator until a dry residue remained. Said residue was colored yellowish brown and 83 g of the solid residue were recovered.

The residue was mixed with 10 l of water and stirred at a temperature of 80° C. for one hour. Thereafter the solution was cooled to 4° C. and the yellowish solution became turbid. Said turbid solution was filtered, for example using a 30 mcm - glass-frit, yielding a clear filtrate.

From said clear filtrate the high molecular constituents, the molecular weight of which was 5000 or higher, were removed using an ultramembrane filter having an exclusion limit of 5000 daltons. The original solution which had to be filtered through said ultramembrane filter had a volume of 10 l and after 8 l of filtrate had been recovered the remaining 2 l were diluted with water until again a volume of 10 l was reached. Said diluted solution was again filtered until 2 l remained, said 2 l again diluted to 10 l and said second diluted solution once again filtrated until 2 l remained.

Said filtration process accordingly yielded 24.1 of a ultrafiltrate which was free of any constituents having a molecular weight of 5000 daltons or higher, e.g. free of proteins having a high molecular weight.

Said filtrate was evaporated under vacuum, until 2 l of a concentrated filtrate remained. Thereafter said concentrated filtrate was lyophilized yielding 79 g of yellow powder.

With said powder, i.e. the concentrate of the extract of the organs of the embryonic calves the pharmaceutical preparations were prepared and the chemical tests performed.

An aqueous solution containing 40 mg per ml of said dry extracts was submitted to the gel electrophoresis. Said test showed that the product in question was free of any proteinous materials having a molecular weight of 5000 daltons or higher.

An aqueous solution containing 40 mg per ml of the dry residue was submitted to an antigen test. Said test was performed with rabbits which prior had been sensibilized to calf serum. In said antigen test the products showed no antigenetic activity. Also the antigen test according to Ouchterlony was performed and also in said test the product in question was free of any antigenetic activity.

EXAMPLE 2

Preparation of pharmaceutical products using the extract of active ingredients recovered according to the process of example 1

Solutions were prepared which can be administered via injection, for example through an intramuscular injection or via infusion.

Said solutions contained the dry extract of the embryonic organs prepared according to example 1 dissolved in water (which had been distilled twice) in a concentration of 40 mg of the dry product per ml. Said solutions were free of pyrogens and sterile.

For the performance of tests for comparison, corresponding placebo-solutions were prepared which contained instead of the extract of embryonic organs 0.9% by weight, referred to the weight of the aqueous solution of sodium chloride dissolved in water which had been distilled twice. Said placebo solutions were also free of pyrogens and sterile.

Furthermore lozenges for the oral administration were prepared which contained per lozenge 200 mg of the dry extract of embryonic organs prepared according to example 1.

Furthermore also placebo-lozenges for the oral administration were prepared, which were used for testing the group of persons for comparison. Said placebo-lozenges were free of the extract of embryonic organs and any other pharmaceutically active ingredients and they contained instead of this 200 mg of lactose per lozenge.

A cream for topical application to the skin was prepared which cream contained per g of the skin-cream base 20 mg of the dry embryonic extract prepared according to example 1. The cream base containing said active ingredient had a neutral pH value and it contained no perfume.

Furthermore a placebo cream was prepared which contained only the corresponding cream base of neutral pH range which did not contain any perfume. Said placebo cream, accordingly, was free of any active ingredient and it was used for the testing of the group of persons for comparison.

EXAMPLE 3

Testing of the activity of mitigating the condition of reduced blood flow through peripheric organs.

Said test was performed applying the recumbent position-test according to Ratschow. In said test the tested person was laying on a tiltable bed and the legs of the tested person were lifted until they were in a vertical position. In said position the tested person performed rolling movements with both feet.

Persons which did not suffer from reduced blood flows through the peripheral blood vessels could remain in said position for ten minutes or longer without having any uncomfortable feeling or pain. Contrary to this with persons who suffered from insufficient blood supply to peripheral organs there could be noticed after a time shorter than 10 minutes that the complexion of the skin of the legs turned to a lighter shade and the persons began to feel pain. The span of time until the persons began to feel the pain was measured and denominated as "pain-point". Only those persons were submitted to further tests which had reached in said preceding tests the point of pain after five minutes or within a still shorter time.

After said pretests the legs of the tested persons were brought to a vertical position, however so, that the feet were on the bottom. Tested persons which did not suffer from reduced blood flow through peripheric organs showed within one or two seconds a turning red of the skin of the legs and after about five seconds the veins were again filled with blood. In persons which suffered from reduced blood flows through peripheric organs the time until the skin turned red was retarded and also the time until the veins were again filled, compared with the corresponding lapse of time measured with persons who did not suffer from a reduced blood flow through peripheric organs.

Totally 50 persons which suffered from reduced blood flow through peripheric organs according to the preliminary test described above were selected and said persons were 50 to 71 years old. From said 50 persons arbitrarily two groups, each comprising 25 persons, were selected and in each of said two groups the number of male persons and female persons was equal.

To the 25 persons of the test group there was administered during six days each day one ml of the solution containing the extract of embryonic organs by intramuscular injection. The next day, i.e. the seventh day after the beginning of the treatment, and until the 36th day the tested persons received no more injections but each day there was administered to the tested persons one lozenge containing as active ingredient the embryonic extract prepared according to example 1.

In the group for comparison to the 25 tested persons there was administered during six days each day 1 ml of the placebo solution by intramuscular injection. Thereafter in said group for comparison to each of the tested persons there was administered from the seventh day after the beginning of the injection treatment until the 36th day each day one placebo lozenge by oral administration.

The recumbant position-test according to Ratschow described at the beginning of said example was performed with the person at the day zero, i.e. before the first injection treatment, at the day seven, i.e. after the last intramuscular injection, and on the day 36, i.e. after the last oral administration of the lozenge.

In the tests performed on the day zero the pain-point was reached with the 25 persons of the test group and with the 25 persons of the group for comparison within 40 seconds to 250 seconds.

The corresponding tests performed on the sixth day after the treatment showed that in the test group the time until the point of pain was reached was clearly prolonged, the average value in said group was 90 seconds later than the average value on the day zero. Contrary to this in the group for comparison the average value was prolonged for only seven seconds (a not significant value) compared with the average value on the day zero.

The corresponding tests performed on the 36th day showed that in the test group the average value of the pain-point was retarded for 210 seconds, compared with the corresponding average value in said group on the day zero. Contrary to this in the group for comparison the average value of the pain-point was retarded for only 10 seconds, referred to the corresponding average value in said group on the day zero.

In the test group before the beginning of the treatment the average time during which the persons could bring their feet to a higher position, until the point of pain was reached, was about two minutes. After the 36th day of the test the average time in said position until the pain-point was reached was in the test group six minutes. In the corresponding test in the group of comparison the average value of the pain-point before the treatment was as well two minutes and after the treatment with the placebo solution respectively the placebo lozenge also two minutes.

EXAMPLE 4

Testing of the blood supply to the brain

Said test was performed using remembrance tests.

On a chess-board there were selected from the total of 64 squares 10 squares using a random number generator. The 10 selected squares were provided in the sequence of A1-H8 with numbers ranging from zero to nine and the numbering of the selected square was again performed using the random number generator. The numbers were noted on paper squares having the same size as the squares of the chess-board and the papers were put onto the corresponding position of the chess-board. Accordingly, each of the randomly selected squares of the chess-board was provided with one number in the range of zero to nine, each number occurring only once, wherein however the position of said numbers was again random.

Each tested person was able to study the randomly distributed numbers on the chess-board for 15 seconds and thereafter the paper squares were turned over so that the person could no longer see the numbers. After 15 seconds each test person was allowed to note on the backside of the paper the number which he had remembered.

The results of said tests were evaluated by comparing the numbers noted by the tested person with the numbers on the chess-board before the papers were turned over. Only the correct number in the correct position was counted as a point.

Each tested person was submitted to the test totally ten times and the tests were performed in intervals of three minutes. In each of said ten tests the selected squares of the chess-board were different and also the randomly selected numbers were different.

40 persons having an age of 60–75 years which all complained that they had difficulties in concentrating themselves and difficulties in remembrance, were submitted to the pretests. In said group of 40 persons about an equal number of men and women were present. From said group all those persons were removed which had reached in the pretests more than 50 points, which accordingly had remembered totally 50% of the possible maximum of 100 numbers.

After said persons with the best remembrance had been removed there remained totally 21 persons, the remembrance of which was worse. Of said 21 persons there was arbitrarily selected a test group of 11 persons and a group for comparison comprising ten persons.

To the 11 persons of the test group there was administered during six days once a day 1 ml of the injectable solution of the embryonic organs described in example 2 by intramuscular injection. After said treatment, i.e. from the seventh day until the 36th day to each person there was administered orally a lozenge described in example 2 which contains the extract of the embryonic organs.

In the group for comparison to the persons there was administered on the days 1–6 each day 1 ml of the placebo solution by intramuscular injection and thereafter from the 7th day to the 36th day of the test there was administered to the person once a day orally one placebo dragée.

The above described remembrance tests were performed with the persons of the test group and with the persons of the group for comparison on the day zero, i.e. before the first treatment, on the day seven, i.e. one day after the last intramuscular injection, and on the day 36, i.e. the last day on which a lozenge had been administered orally.

Of the totally test 21 persons no person reached in the remembrance test on the day zero, i.e. before the first treatment, more than 47 points and the total points reached by each of said persons were in the range of 14 to 47 points.

In the test group on the seventh day the average value of the points had increased by 12.7 points, compared with the average on the day zero. On the day 36 the average value had increased by 18 points, compared with the average value on the day zero.

In the group of comparison the average value of points on the seventh day had increased by 3.4 points, compared with the average value on the day zero. However on the day 36 after the treatment the average value was lower by two points, compared with the average value on the day zero.

The results of said tests show that by an intramuscular administration of the inventive pharmaceutical preparations a clear improvement of the memory and the remembrance could be achieved and subsequent administration of pills containing the extract of the embryonic organs resulted in a still further improvement.

EXAMPLE 5

Tests for controlling acne vulgaris 20 persons being 16–21 years old, who all suffered from a severe acne on the skin of the face, were selected for said test. Ten of the tested persons were female and ten male.

All of the tested persons were treated for 30 days with the placebo cream described in example 2. Before the beginning of said treatment and after said treatment with the placebo cream, a dermatologist determined qualitatively whether the acne remained unaltered, became worse, was improved or whether it had healed completely.

The treatment was thereafter interrupted for sixty days and then the same persons were submitted to a further treatment of 30 days. Now, however, the cream containing the extract of the embryonic organs described in example 2 was administered.

Of the tested persons 12 showed no mitigation of the acne after the treatment with the placebo cream, however a distinct reduction of the acne after the treatment with the cream containing the active ingredients. Two of said persons had no acne at all after they had been treated with the cream containing the active ingredients.

Three of the tested persons showed a decrease of the acne after the treatment with the placebo cream and also a decrease of the acne after the treatment with the cream containing the embryonic extract as active ingredient. With said three persons, however, the acne increased clearly during the time when no cream was applied.

Two of the tested persons showed a reduction of the acne after the treatment with the placebo cream, a clear increase of the acne during the time when no cream was applied and no improvement of the acne during the further treatment with the cream containing the active ingredient.

With two of the tested persons no mitigation of the acne could be achieved, i.e. neither with the treatment with the placebo cream nor with the treatment with the cream containing the embryonic extract as active ingredient.

What is claimed is:

1. In a process for preparing an extract of finely divided embryonic mammalian organs, which is free of non-polar constituents and constituents having a high molecular weight, by treatment with a mixture of water and a water soluble organic solvent, the improvement comprising
   (a) dispersing in said solvent mixture a finely divided embryonic mammalian organ, excluding brains and embryonic glands which produce hormones, said mixture containing at least 70 volume percent of said organic solvent and having a pH of 6–8;
   (b) vigorously stirring and refluxing said dispersion at atmospheric pressure for at least two hours while maintaining said pH;
   (c) cooling the dispersion to a temperature below 8° C.;
   (d) separating the liquid from the solids;
   (e) subjecting said separated liquid to a vacuum to evaporate the liquid leaving a dry residue;
   (f) diluting said residue with water and stirring at a temperature of 75°–85° C. for 30 minutes to 2 hours;
   (g) cooling said diluted residue to a temperature below 8° C. to remove solids and discarding said solids; and
   (h) filtering said cooled diluted residue using an ultramembrane filter to remove any constituents having a molecular weight greater than 5000 daltons.

2. The process of claim 1 in which said solvent mixture contains 75 to 85 volume percent of an organic solvent taken from the group consisting of methanol, ethanol, propanol, and acetone and in which the pH of the dispersion is in the range of 6.5 to 7.5.

3. The process of claim 2 in which said organic solvent is present in the amount of 80 volume percent and the dispersion has a pH in the range of 6.8 to 7.1.

4. The process of claim 2 in which step b is carried out for 2.5 to 3.5 hours and steps c and d are carried out at a temperature of 3° to 5° C.

5. The process of claim 1 wherein one part by weight of fresh, finely divided embryonic organs are dispersed in 5 to 15 parts by weight of said solvent mixture.

6. The process of claim 5 wherein one part by weight of fresh, finely divided embryonic organs is dispersed in 9 to 10 parts by weight of said solvent mixture.

7. The process of claim 2 wherein one part by weight of fresh, finely divided embryonic organs are dispersed in 5 to 15 parts by weight of said solvent mixture.

8. The process of claim 1 or claim 2
   wherein at least two mammalian organs are used and are isolated from embryos recovered after half to 5/6 of the usual gestation period
   said mammalia being taken from the group consisting of ruminants, rodents, horses and swine and
   said embryonic organs are selected from the group consisting of lungs, kidneys, livers and hearts.

9. The process of claim 8 wherein
   5–12 parts by weight of said dry residue of step e are recovered per 1000 parts by weight of said mammalian organ
   in step f one part by weight of said dry residue is diluted with 100–150 parts by weight of water and stirred for about one hour at a temperature in the range of 77°–83° C. and
   step g is performed at a temperature in the range of 2° C. to 6° C.

10. A process as claimed in claim 8 wherein after the evaporation of the aqueous organic solution there remains a yellowish brown dry residue and wherein per 1000 parts by weight of the finely divided fresh embryonic mammalian organs there are recovered 5–12 parts by weight of said dry residue and wherein one part by weight of said dry residue is diluted with 100–150 parts by weight of water and stirred for about one hour at a temperature in the range of 77°–83° C. and thereafter again cooled to a temperature in the range of 2° C. to 6° C. and the solid constituents removed from the solution at said temperature and discarded and thereafter the constituents having a molecular weight of more than 5000 daltons are removed by ultrafiltration using an ultramembrane filter having an exclusion limit of 5000 daltons.

11. The process of claim 5 wherein
   5–12 parts by weight of said dry residue of step e are recovered per 1000 parts by weight of said mammalian organ in step f one part by a weight of said dry residue is diluted with 100-150 parts by weight of water and stirred for about one hour at a temperature in the range of 77°-83° C. and step g is performed at a temperature in the range of 2° C. to 6° C.

12. In a process for preparing an extract of finely divided embryonic mammalian organs, which is free of non-polar constituents and constituents having a high molecular weight, by treatment with a mixture of water and a water soluble organic solvent, the improvement comprising (a) dispersing one part by weight of at least 2 finely divided embryonic mammalian organs recovered after half to 5/6 of the usual gestation period said mammalia being taken from the group consisting of ruminants, rodents, horses and swine, said embryonic organs being taken from the group consisting of lungs, kidneys, livers and hearts in 5 to 15 parts by weight of said solvent mixture said mixture containing 75 to 85 volume percent of an organic solvent taken from the group consisting of methanol, ethanol, propanol and acetone and having a pH of 6.5 to 7.5;

(b) vigorously stirring said dispersion at atmospheric pressure for at least two hours;

(c) cooling said dispersion to a temperature below 8° C.;

(d) separating the liquid from the solids;

(e) subjecting said separated liquid to a vacuum to evaporate the liquid leaving a yellowish brown dry residue;

(f) diluting one part by weight of said dry residue with 100-150 parts by weight of water and stirring for about one hour at a temperature of 77°-83° C.;

(g) cooling said diluted residue to a temperature in the range of 2° to 6° C. to precipitate solids and discarding said solids; and (h) filtering said cooled diluted residue to remove any solids having a molecular weight of more than 5000 daltons using an ultramembrane filter.

13. The process of claim 9 wherein step h is performed using an ultramembrane filter by first filtering ⅔ to 5/6 of the total volume, diluting the not yet filtrated part with water to a volume corresponding to the starting volume, and thereafter filtering ¾ to 5/6 of the diluted material through the ultramembrane filter.

14. The process of claim 1 wherein step h is performed using an ultramembrane filter and the aqueous solution is concentrated under vacuum to produce a dry residue.

15. The extract of mammalian organs which is free of constituents having a high molecular weight and free of non-polar constituents prepared according to the process of claim 1.

16. The extract of mammalian organs which is free of constituents having a high molecular weight and free of non-polar constituents prepared according to the process of claim 12.

17. A pharmaceutical preparation for the treatment of reduced blood flow or the treatment of acne vulgaris which contains as the pharmaceutically active ingredient the extract of claim 15 or 16.

18. A method for treating acne vulgaris comprising the topical application of the extract of claim 15.

* * * * *